US00PP10914P

United States Patent [19]

Pouw

[11] Patent Number: Plant 10,914

[45] Date of Patent: May 25, 1999

[54] HYBRID TEA ROSE PLANT NAMED 'PANPAST'

[75] Inventor: A. A. Pouw, De Kwakel, Netherlands

[73] Assignee: Panorama Roses N.V., Curacao, Netherlands

[21] Appl. No.: 08/920,790

[22] Filed: Aug. 29, 1997

[51] Int. Cl.[6] ..... A01H 5/00

[52] U.S. Cl. ..... Plt./130

[58] Field of Search ..... Plt./11, 18, 16, Plt./17, 130, 131, 137, 138, 136, 135

*Primary Examiner*—Howard J. Locker

*Attorney, Agent, or Firm*—Christie, Parker & Hale, LLP

[57] ABSTRACT

A new variety of hybrid tea rose plant producing light apricot flowers of good form and suitable for growing under glass.

1 Drawing Sheet

BACKGROUND OF THE INVENTION

The present invention relates to a new and distinct variety of rose plant of the hybrid tea rose class which was created by crossing undistributed, unnamed and unpatented seedlings as seed and pollen parents in Quito, Ecuador. The varietal denomination of the new variety is 'PANPAST'. The new variety was isolated and asexually reproduced by budding in Ecuador.

SUMMARY OF THE INVENTION

Among the novel characteristics possessed by this new variety which distinguish it from its parents and all other varieties of which I am aware are its attractive light apricot flowers of good form with long stems borne on a floriferous plant and suitable for production of cut flowers under glass. The new variety has been reproduced through propagation by cuttings, grafting, budding and micropropagation.

Asexual reproduction by budding of the new variety as performed in Quito, Ecuador, shows that the foregoing and other distinguishing characteristics come true to form and are established and transmitted through succeeding propagations.

BRIEF DESCRIPTION OF ILLUSTRATION

The accompanying illustration shows a typical specimen of the vegetative growth and flower of the new variety depicted in color as nearly true as it is reansonably possible to make the same in a color illustration of this character.

DESCRIPTION OF THE NEW VARIETY

The following is a detailed description of the new variety, with color terminology in accordance with The Royal Horticultural Society Colour Chart (R.H.S.C.C.) and horticultural terminology in accordance with standard terminology used in UPOV-approved horticultural guidelines. The terminology used in color descriptions herein refers to plate numbers in the aforementioned color chart. Phenotypic expression may vary depending upon growing conditions under different climate, soil, and cultivation conditions.

Parentage: Seed and pollen parents are unnamed seedlings.
Class: Hybrid Tea.

The following further horticultural description is based on observations made of specimens grown under glass in Quito, Ecuador.

Flower

Blooming habit: Nearly continuous, about 200 stems/m$^2$/year.

A. Bud:

(1) *Size.*—Medium, about 1 to 2 inches long by about 1 to 1.5 inches wide, before sepals separate.

(2) *Form.*—Ovate (shape of longitudinal section just before separation of sepals); urn-shaped after sepals part and petals begin to separate.

(3) *Color.*—At initial separation of sepals, near 15C to 15D; after sepals separate near 36D with occasional red streaks or blush and red tip.

(4) *Sepals.*—Longer than bud, some foliaceous; purple, near 136C to 137C on top surface, some with dark green or purplish ends, near 137B undersurface.

(5) *Peduncle.*—Long, about 7 cm. Strength-erect, strong. Color-medium green, near 137C to 137D with brownish tinge.

B. Flower: Medium; viewed from above — star-shaped; viewed from side — (a) upper part of fully opened flower, convex; (b) lower part of fully opened flower, flat.

(1) *Size.*—Average size when fully expanded — about 3 inches at about ⅓ to ½ open, about 10 cm to 11.5 cm fully open.

(2) *Borne.*—Singly, one to a stem.

(3) *Form.*—Pointed center, spiral imbricated, some outer petals ruffled; some inner petals reflex to points, flat top.

(4) *Petalage.*—Fully double, about 15 petals and about 10 petaloids (same color).

(5) *Color.*—After sepals part and petals unfurl color of petal top surface appears near 35D to 36B; inner petals display color near 22C to 22D, especially when petals bunch, with slight pink to red cast in center. Petal undersurface tends to near 55D with yellow/apricot coloring toward point of petal attachment. Color at point of petal attachment is near 11B. Overall tonality from a distance is attractive light apricot; open bloom, petal underside near 56C; middle coloration near 56C to 56D; petal upperside margin coloration near 56A; middle coloration near 56C; flower under margin coloration near 19C; under middle coloration near 16D; upper margin coloration near 19B; upper middle coloration near 16B.

(6) *Peduncle.*—Very slight roughness.

(7) *Fragrance.*—Absent or weak.

(8) *Length of stems.*—About 50 to 100 cm.

Petals:

(1) *Texture.*—Crisp.

(2) *Appearance.*—Inside velvety and outside satiny.

(3) *Form and size.*—Broad, medium, medium undulation of margin.

(4) *Arrangement.*—Regularly arranged, imbricated.

(5) *Petaloids.*—Several.

(6) *Lasting quality.*—Long-lasting quality on plant and after cutting, about 14 days.

Reproductive Organs

A. Stamens, filaments and anthers:

*Arrangement and color.*—Regularly arranged around styles; color of filaments — yellow.

B. Pollen:

*Color.*—Near 19B.

C. Styles: Long, stigma above mouth of receptacle, pale yellow.

D. Stigmas: Yellow, positioned below anthers.

E. Hip: Pitcher-shaped; medium seed vessel at petal fall.

Plant

A. Form: Narrow, bushy, average disease resistance; height about 178 cm, spread about 50 cm.

B. Growth: Vigorous.

C. Foliage: Compound 3, 5 and 7 leaflets.

(1) *Size.*—3-leaflet leave, terminal leaflet about 4 inches long; 5-leaflet leaves, terminal leaflet about 3 inches long; 7 leaflet leaves, terminal leaflet about 2 inches long.

(2) *Quantity.*—Abundant.

(3) *Color.*—Juvenile foliage — upper side near 183A to 183B; underside near 185A, weak anthocyanin coloration, (shoot about 3 inches long); mature leaf color — upper side near 139A, underside near 138A.

(4) *Shape.*—Broad oval.

(5) *Texture.*—Upper side is weak to medium glossy; underside is matte.

(6) *Edge.*—Serrate.

(7) *Serration.*—Ordinary, acuminate apices.

(8) *Leaf stem.*—Color — near 147A.

(9) *Stipules.*—Short, simple, medium green.

(10) *Leaflets.*—Cross section — flat: absent or weak undulation of margin; terminal leaflet — medium length and medium width; obtuse base.

D. Wood:

(1) *New wood.*—Color — young shoots have weak anthocyanin; coloration — bronze red purple to reddish brown.

(2) *Old wood.*—Color — near 147A to 147B.

E. Prickles (thorns):

(1) *Prickles.*—Present. Shape of lower side — concave; Quantity — short prickles absent or very few, long prickles ordinary; Color — near 173A; Position — irregular.

What is claimed is:

1. A new and distinct rose plant of the variety substantially as shown and described.

* * * * *

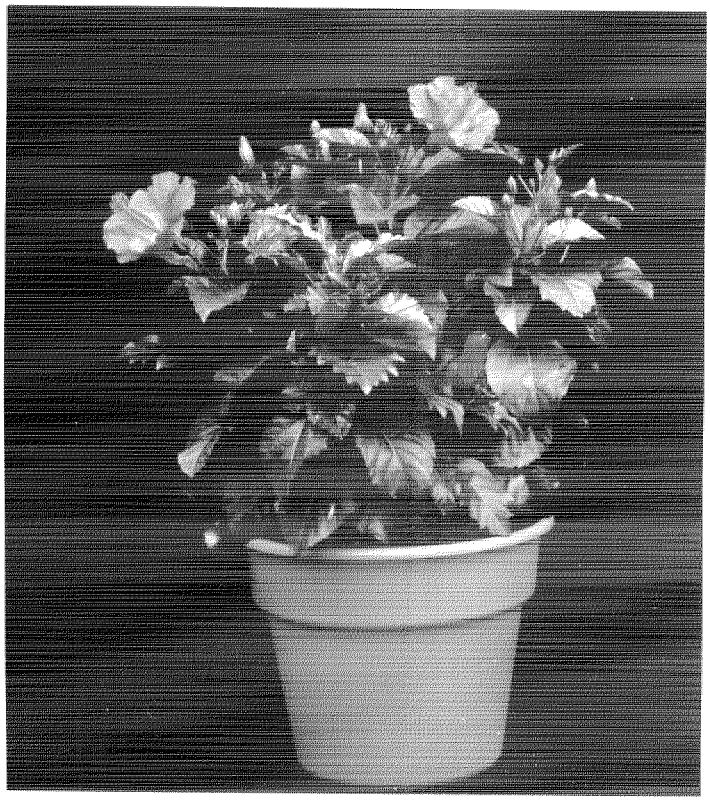
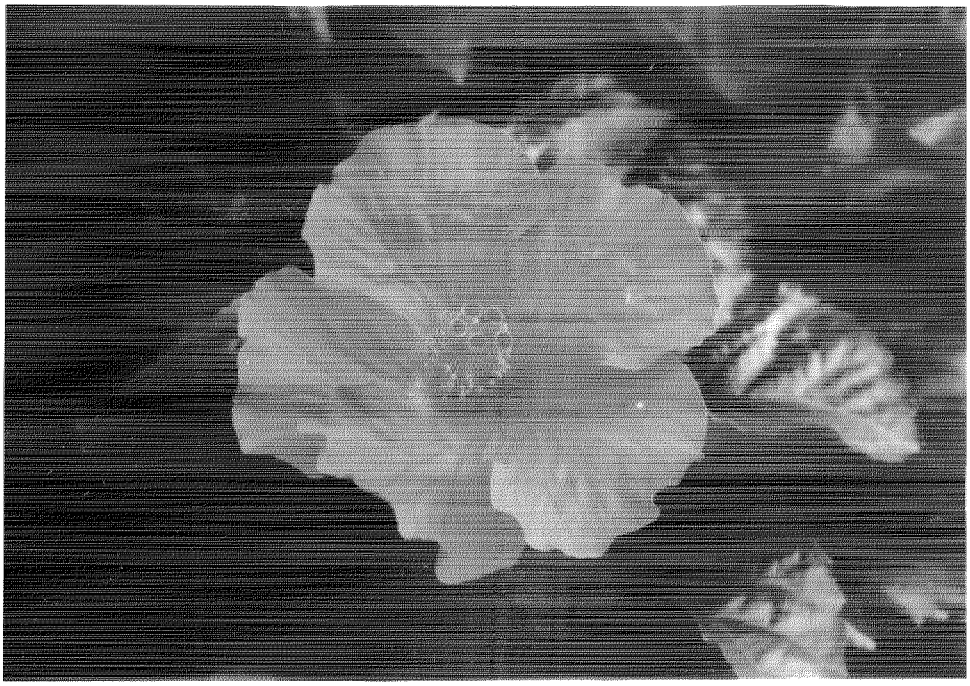

UNITED STATES PATENT AND TRADEMARK OFFICE

CERTIFICATE OF CORRECTION

PATENT NO. : PP 10,914
APPLICATION NO. : 08/920790
DATED : May 25, 1999
INVENTOR(S) : A. W. Pouw It is certified that error appears in the above-identified patent and that said Letters Patent is hereby corrected as shown below:

DELETE Drawing Sheet SUBSTITUTE therefor the Drawing Sheet shown on the attached page.

Signed and Sealed this

Third Day of February, 2009

John Doll

JOHN DOLL
*Acting Director of the United States Patent and Trademark Office*

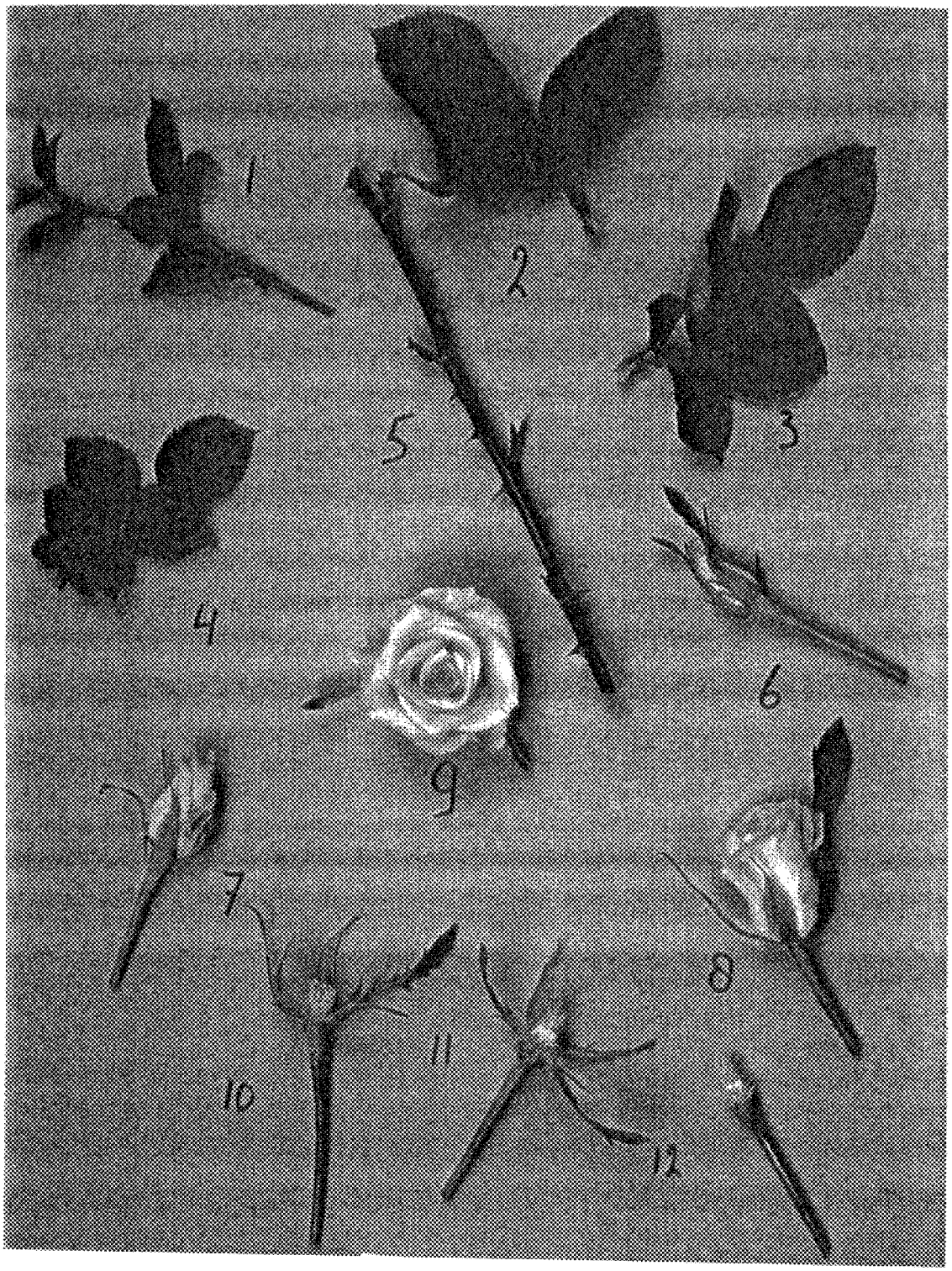
1
2
3
4
5
6
7
8
9
10
11
12

UNITED STATES PATENT AND TRADEMARK OFFICE

CERTIFICATE OF CORRECTION

PATENT NO. : PP 10,914
APPLICATION NO. : 08/920790
DATED : May 25, 1999
INVENTOR(S) : A. A. Pouw It is certified that error appears in the above-identified patent and that said Letters Patent is hereby corrected as shown below:

DELETE Drawing Sheet SUBSTITUTE therefor the Drawing Sheet shown on the attached page.

This certificate supersedes the Certificate of Correction issued Februay 3, 2009.

Signed and Sealed this

Seventh Day of April, 2009

JOHN DOLL
*Acting Director of the United States Patent and Trademark Office*

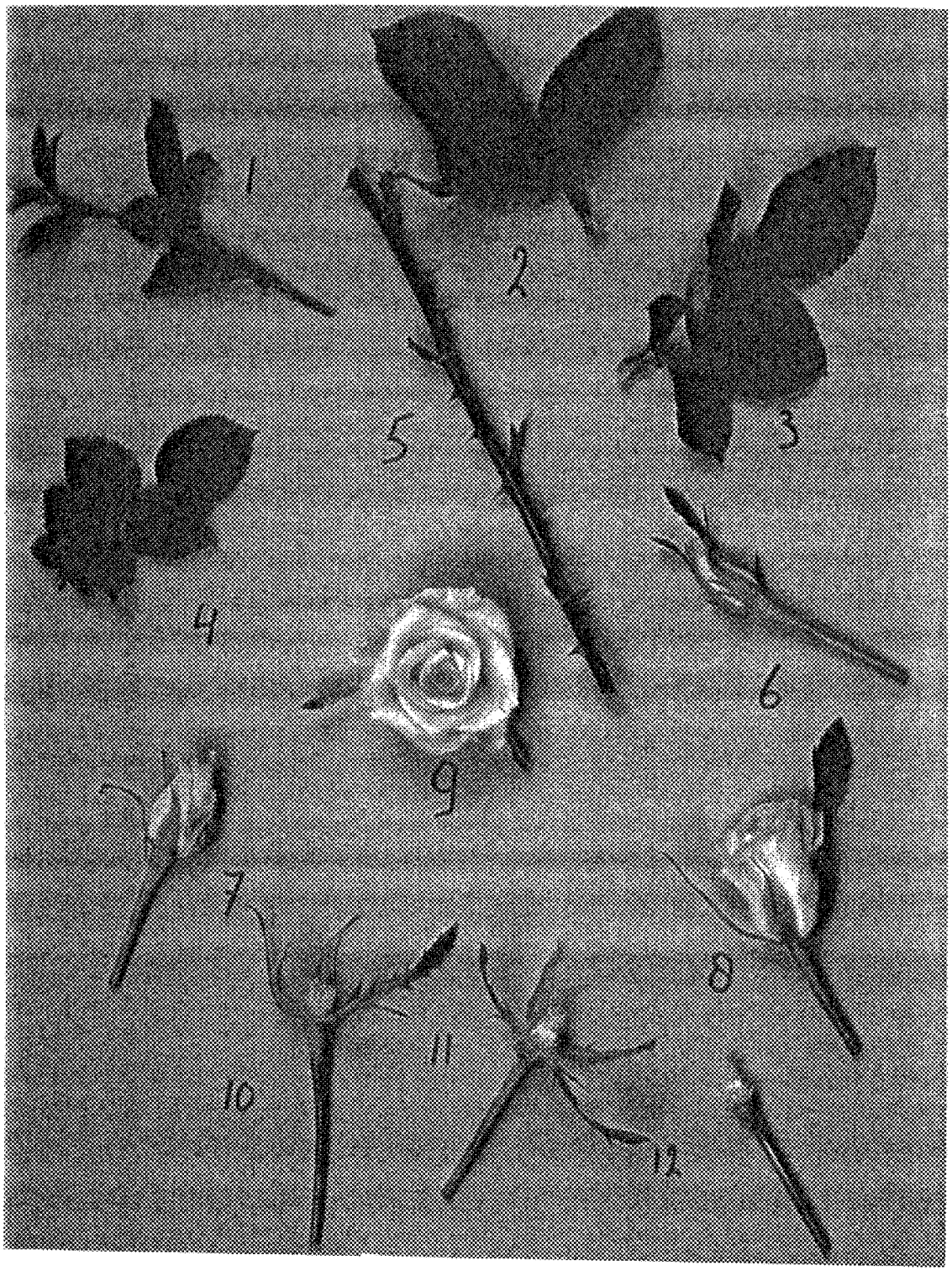
1
2
3
4
5
6
7
8
9
10
11
12